(12) United States Patent
Firouzbakht et al.

(10) Patent No.: US 8,140,377 B2
(45) Date of Patent: Mar. 20, 2012

(54) SYSTEM FOR PREDICTIVE ANALYTICS USING REAL-WORLD PHARMACEUTICAL TRANSACTIONS

(75) Inventors: Reza Firouzbakht, Redmond, WA (US); Elizabeth O. Coulton, Charleston, SC (US); Henry Lai, Milpitas, CA (US); Tigran Markaryan, Reston, VA (US)

(73) Assignee: Accenture Global Services Limited, Dublin (IE)

( * ) Notice: Subject to any disclaimer, the term of this patent is extended or adjusted under 35 U.S.C. 154(b) by 591 days.

(21) Appl. No.: 12/172,386

(22) Filed: Jul. 14, 2008

(65) Prior Publication Data
US 2009/0276287 A1    Nov. 5, 2009

Related U.S. Application Data

(60) Provisional application No. 61/049,914, filed on May 2, 2008.

(51) Int. Cl.
  *G06Q 40/00* (2006.01)
(52) U.S. Cl. ............................. 705/7.29; 705/10; 705/35
(58) Field of Classification Search ................ 705/7, 10, 705/35
  See application file for complete search history.

(56) References Cited

U.S. PATENT DOCUMENTS

| 6,556,992 B1 | 4/2003 | Barney et al. | |
| 7,653,568 B2 | 1/2010 | Keller et al. | |
| 7,860,770 B2 * | 12/2010 | Ciampi et al. | 705/35 |
| 2004/0030592 A1 * | 2/2004 | Buck et al. | 705/10 |
| 2005/0209946 A1 * | 9/2005 | Ballow et al. | 705/35 |
| 2007/0106550 A1 * | 5/2007 | Umblijs et al. | 705/10 |

FOREIGN PATENT DOCUMENTS

WO    WO 03042898 A2 *    5/2003

OTHER PUBLICATIONS

Patricia M. Danzon et al., "Productivity in Pharmaceutical-Biotechnology R&D: The Role of Experience and Alliances", Mar. 2003, 39 pgs.*
Arora et al., "The Nature and the Extent of the Market for Technology in Biopharmaceuticals", MPRA, EPRIS Annual Meeting, London, Dec. 15-16, 2000, 43 pgs.*

* cited by examiner

*Primary Examiner* — Asfand Sheikh
*Assistant Examiner* — Hunter Wilder
(74) *Attorney, Agent, or Firm* — Brinks Hofer Gilson & Lione (57) ABSTRACT

A system for predictive analytics using real-world pharmaceutical transactions includes a computer having a processor and memory, a data collection component configured to aggregate data for a plurality of pharmaceutical transactions, and a data reduction module configured to eliminate non-compliant transactions to generate a reduced transaction data set. An analysis module applies multiple linear regression analysis to a portion of the reduced transaction data set to identify key regression variables that correlate with an excess total return to shareholders. The analysis module also applies logistic regression analysis to a portion of the reduced transaction data set to identify key regression variables that correlate with an increased probability of regulatory agency approval. A report generator provides a graphical output of the identified key regression variables and a probability value corresponding to a likelihood of regulatory agency approval.

18 Claims, 6 Drawing Sheets

SYSTEM FOR PREDICTIVE ANALYTICS USING REAL-WORLD PHARMACEUTICAL TRANSACTIONS

CROSS-REFERENCE TO RELATED APPLICATIONS

This application claims the benefit of priority from co-pending provisional patent application Ser. No. 61/049,914, filed on May 2, 2008, entitled System For Predictive Analytics Using Real-World Pharmaceutical Transactions. Application Ser. No. 61/049,914 is hereby incorporated by reference in its entirety.

BACKGROUND OF THE INVENTION

1. Technical Field

This disclosure relates to predictive analytics in the pharmaceutical industry. In particular, this disclosure relates to predicting the likelihood of success of a real-world pharmaceutical transaction based on analysis of prior pharmaceutical transactions.

2. Background

Pharmaceutical companies often venture outside of their own organizations in search of new assets to develop in their pipeline and to ultimately bring to market. These deals may be in the form of a purchase, license, joint development, strategic arrangement, or other business transaction. However, the key factors and conditions that predict and quantify a successful business transaction or relationship have not been established. Typically, pharmaceutical industry experts have relied on relationships, qualitative evidence, intuition, or experience-based "rules of thumb" when establishing licensing programs or collaborative arrangements. However, there has been no quantitative evidence to prove that any of these techniques are successful in selecting deals that create more value. Reliance on such factors does not necessarily increase the probability that the transaction will be successful. An unmet need exists to identify and quantify the factors and conditions that correspond to successful pharmaceutical business transactions or relationships.

The pressure on pharmaceutical companies to achieve high performance and deliver new products has never been greater. With revenues eroding because of expiring patents and generic competition, companies are in a collective scramble to acquire new compounds. In search of the next innovation, companies have been through a decade of whirlwind deal-making to bring in products from external sources. Whether through licensing or more elaborate business development investments, the number and value of these deals are only expected to increase.

However, only a small portion of these deals result in successful products. To increase the success of these efforts to feed the pipeline, companies have two strategic options. The pharmaceutical companies can either engage in more deals, or they can become increasingly selective and engage in fewer deals. The pharmaceutical industry now relies heavily on the first strategy—raising its level of investment in the hope of yielding a higher absolute number of successful products. Because there are limited resources for investing in new deals, there is a need for a tool that can assist pharmaceutical companies to be more selective, and to engage in fewer deals that have a higher probability of successful returns.

SUMMARY

The system and method for predictive analytics using real-world pharmaceutical transactions addresses a second option, namely increasing selectivity in the business development deals a company makes, by identifying the characteristics that make a deal most likely to succeed. One embodiment of a system for predictive analytics using real-world pharmaceutical transactions includes a computer having a processor and memory, a data collection component configured to aggregate data for a plurality of pharmaceutical transactions where the aggregate data corresponds to publicly-traded financial data based upon a predetermined time period surrounding a public announcement of the respective pharmaceutical transaction.

A data reduction module eliminates non-compliant transactions to generate a reduced transaction data set and an analysis module applies multiple linear regression analysis to a portion of the reduced transaction data set to identify key regression variables that correlate with an excess total shareholder return. The key regression variables that were statistically significant in this analysis were drug development phase, deal type, compound or drug type, and therapeutic area. The analysis module also applies logistic regression analysis to a portion of the reduced transaction data set to identify key regression variables that correlate with an increased probability of regulatory agency approval. A report generator provides a graphical output of the identified key regression variables and a probability value corresponding to a likelihood of regulatory agency approval.

Other embodiments of systems, methods, features, and their corresponding advantages will be, or will become, apparent to one with skill in the art upon examination of the following figures and detailed description. It is intended that all such additional systems, methods, features, and advantages be included within this description, be within the scope of the invention, and be protected by the following claims.

BRIEF DESCRIPTION OF THE DRAWINGS

The system may be better understood with reference to the following drawings and the description, in addition to the presentation sheets included in the appendix, which is incorporated herein in its entirety. The components in the figures are not necessarily to scale, emphasis instead being placed upon illustrating the principles of the invention. Moreover, in the figures, like-referenced numerals designate corresponding parts throughout the different views.

DETAILED DESCRIPTION OF THE PREFERRED EMBODIMENTS

Figure 1:
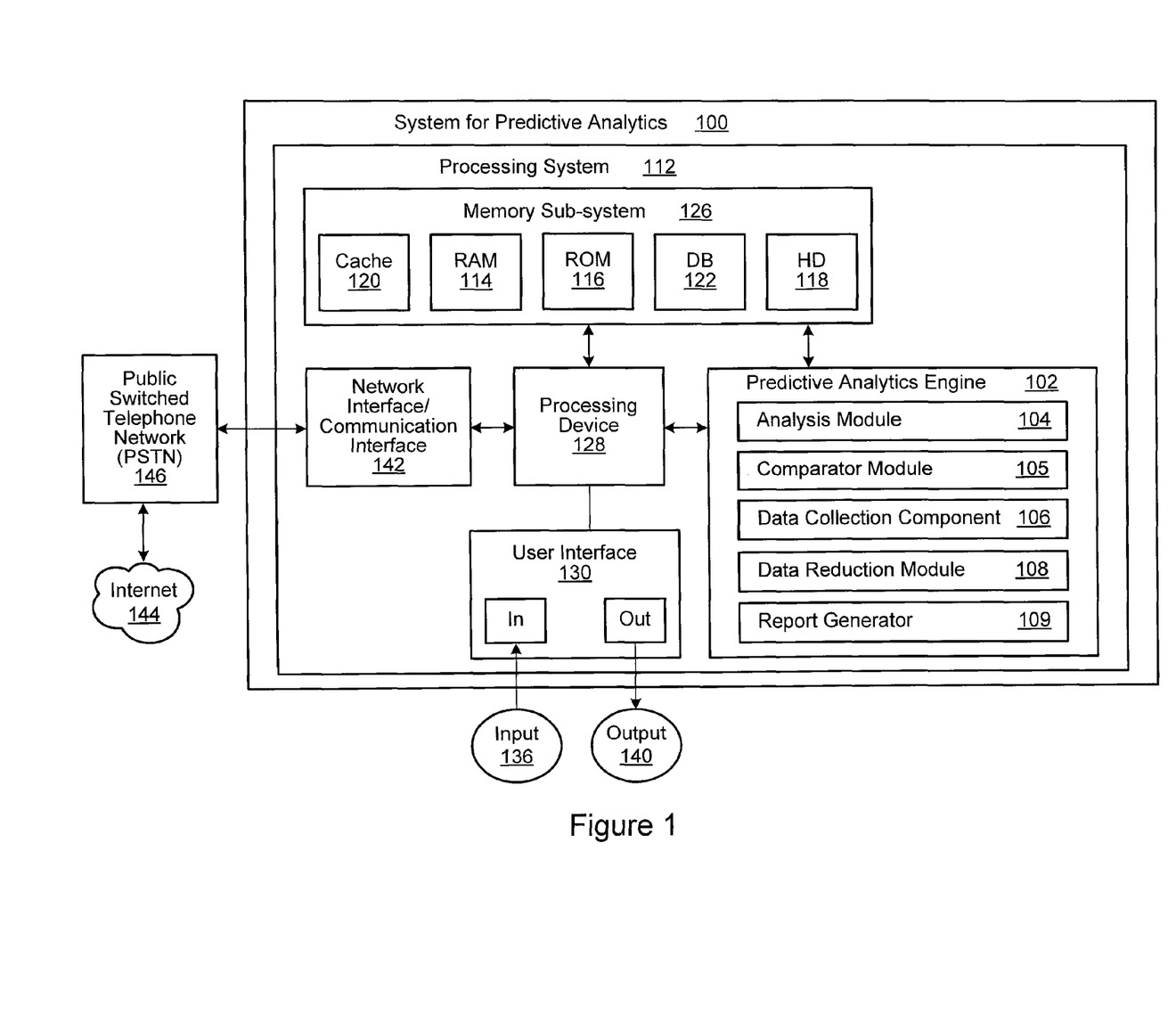
FIG. 1 shows a computing platform and environment.

As shown in FIG. 1, a system 100 for predictive analytics using real-world pharmaceutical transactions provides a platform for applying a statistically rigorous process that identifies "deal" or transaction characteristics that are likely to predict success. The specific embodiment of FIG. 1 is a high-level hardware block diagram of a computer system on which the system 100 for predictive analytics using real-world pharmaceutical transactions may be implemented. The system 100 for predictive analytics using real-world pharmaceutical transactions may be embodied as a system cooperating with computer hardware components and/or as a computer-implemented method.

The system 100 includes a predictive analytic engine or processor 102, which in turn, includes an analysis module 104 or processor, a comparator module 105, a data collection component 106, a data reduction module 108, and a report generator 109. The predictive analytic engine 102 may be a hardware component and/or may performed processes in hardware, software, or a combination of hardware and software. The system 100 includes a computer or processing system 112, which includes various hardware components, such as RAM 114, ROM 116, hard disk storage 118, cache memory 120, database storage 122, and the like (also referred to as "memory subsystem" 126). The computer system 112 may include any suitable processing device 128, such as a computer, microprocessor, RISC processor (reduced instruction set computer), CISC processor (complex instruction set computer), mainframe computer, work station, single-chip computer, distributed processor, server, controller, microcontroller, discrete logic computer, and the like, as is known in the art. For example, the processing device 128 may be an Intel Pentium® microprocessor, x86 compatible microprocessor, or equivalent device.

The memory subsystem 126 may include any suitable storage components, such as RAM, EPROM (electrically programmable ROM), flash memory, dynamic memory, static memory, FIFO (first-in first-out) memory, LIFO (last-in first-out) memory, circular memory, semiconductor memory, bubble memory, buffer memory, disk memory, optical memory, cache memory, and the like. Any suitable form of memory may be used whether fixed storage on a magnetic medium, storage in a semiconductor device, or remote storage accessible through a communication link. A user or system manager interface 130 may be coupled to the computer system 112 and may include various input devices 136, such as switches selectable by the system manager and/or a keyboard. The user interface also may include suitable output devices 140, such as an LCD display, a CRT, various LED indicators, and/or a speech output device, as is known in the art.

To facilitate communication between the computer system 112 and external sources, a communication interface 142 may be operatively coupled to the computer system. The communication interface 142 may be, for example, a local area network, such as an Ethernet network, intranet, Internet, or other suitable network 144. The communication interface 142 may also be connected to a public switched telephone network (PSTN) 146 or POTS (plain old telephone system), which may facilitate communication via the Internet 144. Dedicated and remote networks may also be employed, and the system may further communicate with external exchanges and sources of information 146. Any suitable commercially-available communication device or network may be used.

Figure 2:
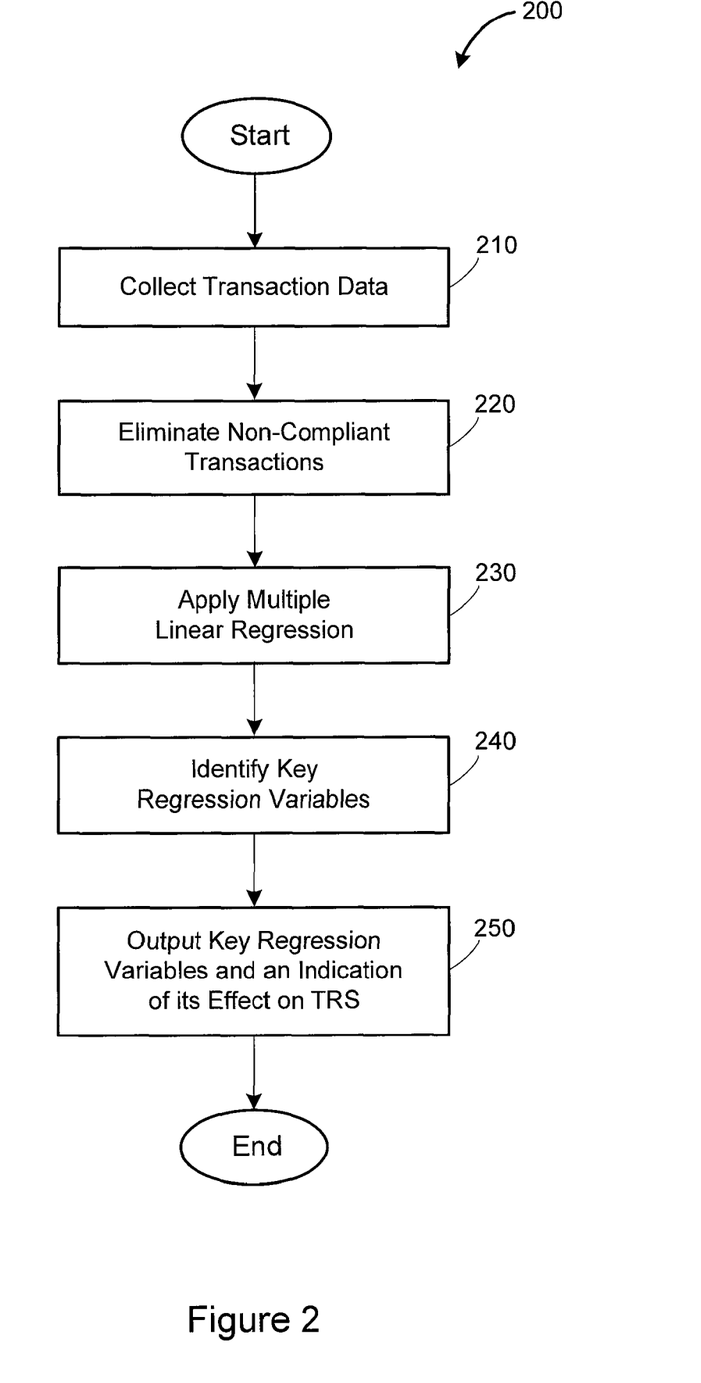
FIG. 2 is a flowchart showing a process identifying key regression variables that correlate with an excess total return to shareholders.

FIG. 2 is a flowchart showing a process (Act 200) that identifies variables that that correlate with an excess total return to shareholders. The process shown, for example in FIG. 2, may be performed by the predictive analytics engine 102. Data for a plurality of pharmaceutical transactions is collected (Act 210), and non-compliant transactions are eliminated (Act 220) to generate a reduced transaction data set. Multiple linear regression analysis is applied to a portion of the reduced transaction data set (Act 230) to identify key regression variables that correlate with an excess total return to shareholders (Act 240). A report is output (Act 250) that provides a graphical output of the identified key regression variables and an indication of the corresponding effect on total return to shareholders.

Figure 3:
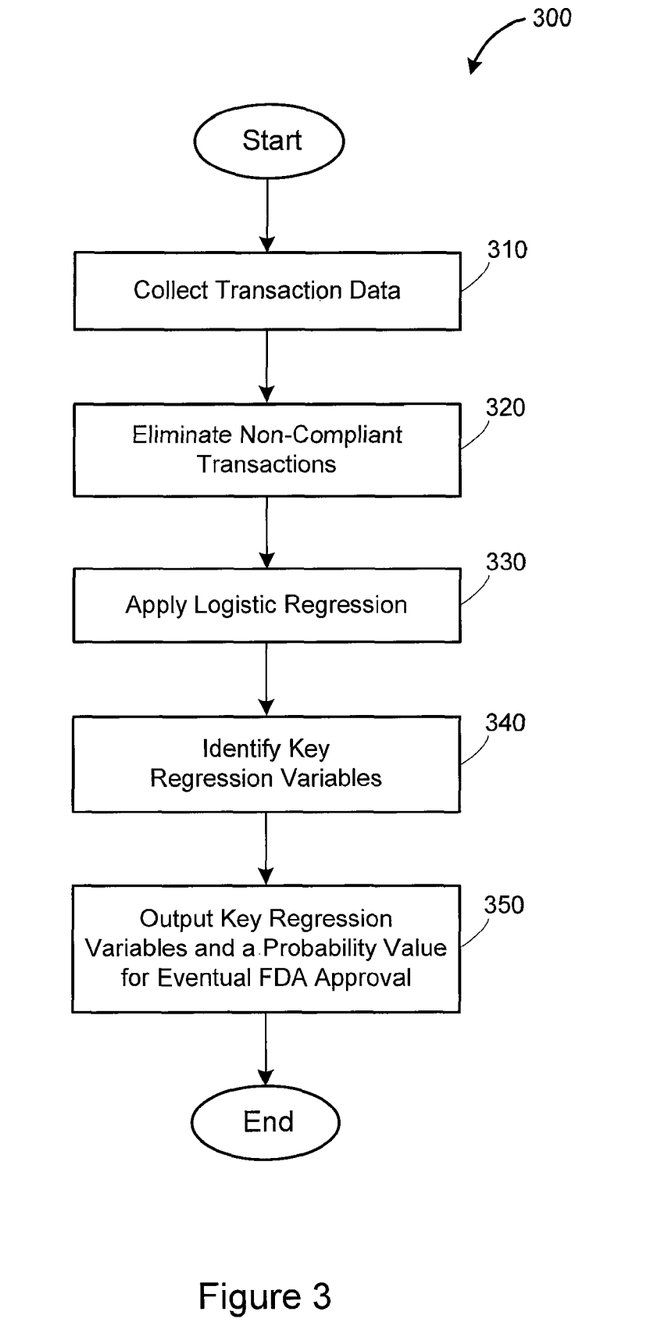
FIG. 3 is a flowchart showing a process predicting the likelihood of eventual FDA approval.

FIG. 3 is a flowchart showing a process (Act 300) that determines a probability that a pharmaceutical deal will result in eventual FDA approval. The process shown, for example in FIG. 3, may be performed by the predictive analytics engine 102. Data for a plurality of pharmaceutical transactions is collected (Act 310), and non-compliant transactions are eliminated (Act 320) to generate a reduced transaction data set. Logistic regression analysis is applied to a portion of the reduced transaction data set (Act 330) to identify key regression variables that correlate with an increased probability of obtaining eventual FDA approval (Act 340). A report is output (Act 350) that provides a graphical output of the identified key regression variables and a probability value corresponding to a likelihood of regulatory agency approval.

Several factors or predictors can indicate which external sourcing arrangements or deal has the best prospects of becoming a winner. In one specific embodiment, the term "success" may be identified based on two separate criteria. A first measure of success is defined as a deal that increases shareholder value (excess total return to shareholders (TRS) or ETRS). "Excess" total return to shareholders may be defined as the 11-day compounded TRS (as defined by CRSP) minus the 11-day compounded TRS of a corresponding index. In one embodiment, the normal return is defined as the TRS AMEX pharma for a pharmaceutical company and AMEX biotech for a biotech company. An 11-day window is a common time frame used in financial transactions because 11 days is believed to be an adequately long window for capturing the market's reaction to the event, namely the announcement of the deal, while still being sufficiently short so as to limit the impact of other corporate events. Data points may be omitted where other major events occurred during the 11-day window. Other timeframes may be used, such as a week, a month, a quarter, or a year.

A second measure of success is defined as a deal that results in eventual FDA (Food and Drug Administration) or other regulatory body approval of the drug compound that is the subject of the deal. Preferably, deals where the drug under evaluation are approved or terminated are analyzed. Deals with ongoing research or pending FDA approval are excluded. Analysis (logistic regression) for Phase I deals are excluded because few Phase I compounds have received approval from the FDA.

In one embodiment, the predictive analytics engine 102 applies regression analysis (multiple linear regression and logistic regression) to identify factors that correlate with a deal's success. Many factors were investigated and analyzed. Such factors may include:

1. Company Acquiring Asset Party Type (CAA)
2. Company with Asset Party Type (CWA)
3. Parties CAA/CWA
4. New Deal Type
5. Size
6. Weakness of Incentive (Upfront Amount divided by Deal Size)
7. Stage of Compound(s)
8. Therapeutic Area
9. Biologic/Small Molecule/Other
10. Transaction # with same partner
11. Prior Relationship with Partner
12. Total Transaction Frequency CAA
13. Total Transaction Frequency CWA The predictive analytics engine 102 identified four predictors of a deal's success based on regression analysis of the above-enumerated factors. The four predictors or "key regression variables" are applicable to the first measure of success (TRS) and to the second measure of success (eventual FDA approval), and include:
1. Phase of Development of the Compound
2. Deal Type
3. Compound Type (Small or Large Molecule)
4. Therapeutic Area The predictive analytics engine 102 includes the analysis module 104 or engine configured to analyze real-world data. The analysis module 104 may apply a multiple linear regression process to measure or determine the occurrence and magnitude of "excess" total return to shareholders (TRS) for both the buyer and the seller (the first measure of success). This process may identify predictors of success, e.g., a higher excess total return to shareholders, as certain factors are determined to be statistically significant through the analysis. For example, in one embodiment, several factors were determined to be the key predictors of success. In another embodiment, analysis may be bounded by an 11-day window around the deal announcement (five days before and five days after). The analysis module 104 may then apply a logistic regression process to determine the type of deal that positively correlates with FDA approval (the second measure of success).

Different regression processes may be used to analyze the data for either the multiple linear regression process (first measure of success-excess total return to shareholders) or the logistic regression process (second measure of success-eventual FDA approval). For example, regression trees, Chi-squared regression, least squares regression, regression sum of sequences, error sum of sequences, orthogonal regression, and other regression processes and techniques may be used.

By way of background regarding the first predictor (phase), Phase I compounds relate to clinical trials that are in the FDA phase I of clinical testing in human subjects. Normally, a small (20-80) group of healthy volunteers is selected. This phase includes trials designed to assess the safety (pharmacovigilance), tolerability, pharmacokinetics, and pharmacodynamics of a drug. These trials are often conducted in an in-patient clinic, where the subject can be observed by full-time staff. The subject who receives the drug is usually observed until several half-lives of the drug have passed. Phase I trials also normally include dose-ranging, referred to as dose escalation, which determines the appropriate dose for therapeutic use. The tested range of doses will usually be a fraction of the dose that causes harm in animal testing. Phase I trials most often include healthy volunteers. However, there are some circumstances when real patients are used, such as patients who have end-stage disease and lack other treatment options. This exception to the rule most often occurs in oncology (cancer) and HIV drug trials. Volunteers are paid an inconvenience fee for their time spent in the volunteer centre. Pay ranges from a small amount of money for a short period of residence, to a larger amount depending on the length of participation.

Once the initial safety of the study drug has been confirmed in Phase I trials, Phase II trials are performed on larger groups (20-300) and are designed to assess how well the drug works, as well as to continue Phase I safety assessments in a larger group of volunteers and patients. The development process for a new drug usually fails during Phase II trials when the drug is discovered not to work as planned, or if it is discovered to have toxic effects. Phase II studies are sometimes divided into Phase IIA and Phase IIB. Phase IIA is specifically designed to assess dosing requirements (how much drug should be given), whereas Phase IIB is specifically designed to study efficacy (how well the drug works at the prescribed dose(s)). Some trials combine Phase I and Phase II, and test both efficacy and toxicity. Some Phase II trials are designed as case series to demonstrate a drug's safety and activity in a selected group of patients. Other Phase II trials are designed as randomized clinical trials, where some patients receive the drug/device and others receive placebo/standard treatment. Randomized Phase II trials have far fewer patients than randomized Phase III trials.

Phase III studies are randomized controlled multi-center trials on large patient groups (300-3,000 subjects or more depending upon the disease/medical condition studied) and are aimed at being the definitive assessment of how effective the drug is, in comparison with current "gold standard" treatment. Because of their size and comparatively long duration, Phase III trials are the most expensive, time-consuming and difficult trials to design and run, especially in therapies for chronic medical conditions. It is common practice that certain Phase III trials will continue while the regulatory submission is pending at the appropriate regulatory agency. This allows patients to continue to receive possibly lifesaving drugs until the drug can be obtained by purchase. Other reasons for performing trials at this stage include attempts by the sponsor at "label expansion" (to show the drug works for additional types of patients/diseases beyond the original use for which the drug was approved for marketing), to obtain additional safety data, or to support marketing claims for the drug. While not required in all cases, it is typically expected that there be at least two successful Phase III trials, demonstrating a drug's safety and efficacy, in order to obtain approval from the appropriate regulatory agencies. The above description of Phase I-Phase III may be found at http://en.wikipedia.org/wiki/clinical_trial.

With respect to the first predictor involving TRS (first measure of success), the market clearly rewards buyers of Phase III compounds with a prediction confidence level "p" where p=0.09. Defining what is statistically significant depends on what the real-life occurrence is expected to be, and what is normally accepted in the industry. In one embodiment, a value of $p<=0.10$ is considered statistically significant, $0.10<p<=0.20$ is considered moderately significant, and $p>0.20$ is considered marginally significant. The market may react in this way because Phase III compounds are closer to generating cash flows. Because these products are scarce, they are highly coveted. But this higher shareholder return for Phase III compounds does not predict FDA approval, which is a surprising and unexpected result of the analysis. In fact, many Phase III compounds whose buyers were richly rewarded by the market failed to receive FDA approval. The lack of correlation between the increase in shareholder value for Phase III compounds and FDA approval may indicate that the market is not adequately differentiating these products. The market is so eager for near-term cash flows that it assumes all Phase III products have roughly equal probability of approval, when in reality they do not.

Figure 4:
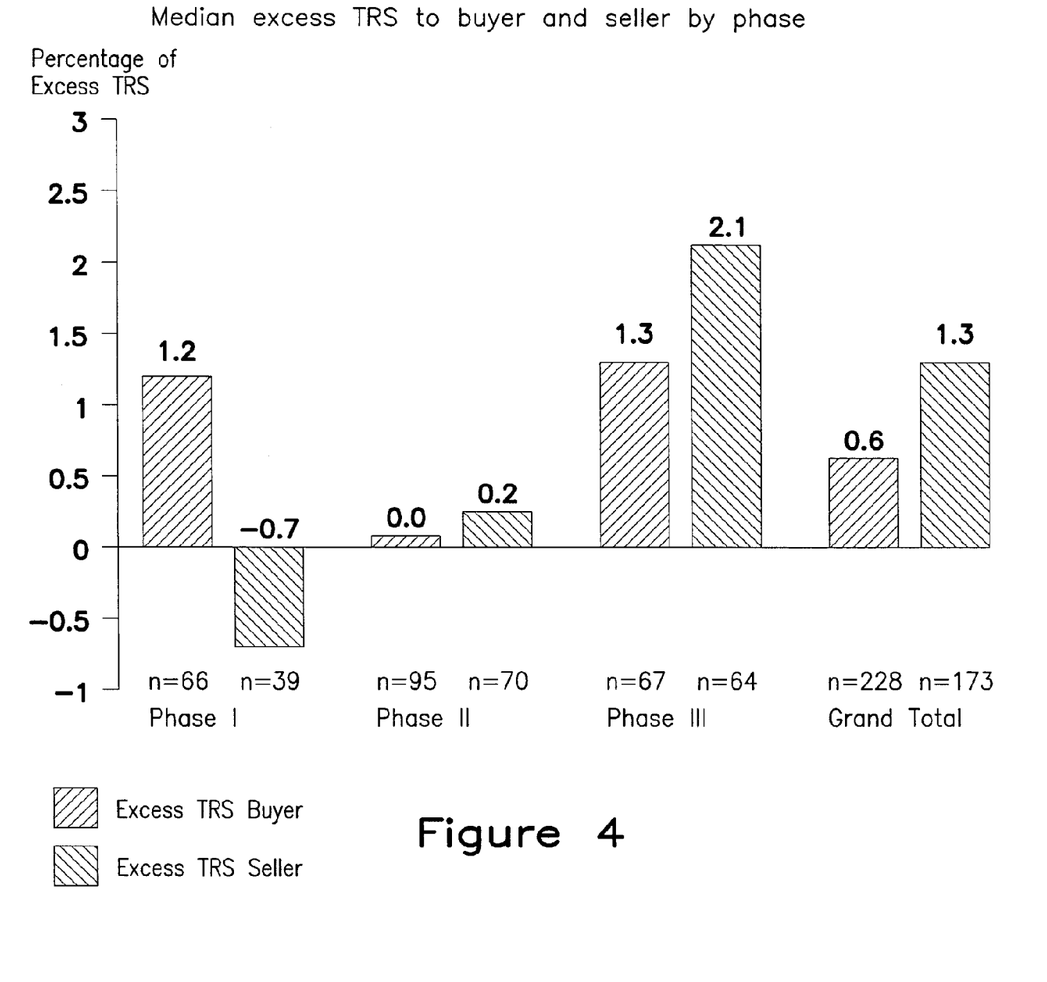
FIG. 4 is a bar chart showing median excess TRS to buyer and seller by clinical phase.

For Phase II deals, a much stronger link exists between market reaction at deal announcement and the likelihood of FDA approval. This suggests that Phase II deals with higher TRS at the deal announcement have a higher probability of being approved. FIG. 4 shows the excess TRS to buyers as the left-hand bar of each pair of bars and the excess TRS to sellers as the right-hand bar in each pair of bars.

With respect to the second predictor, the type of deal is shown in Table 2 below ranging from a less complex deal to a more complex deal.

TABLE 2

Deal type: simple to complex

| | Deal Type | Definition | Examples |
|---|---|---|---|
| More Complex ↑ | Competitive Collaboration | Two companies working together for the purpose of executing a particular business undertaking, but are also in competition with each other in the same market (usually collaboration in commercialization) | Amgen/Wyeth with Enbrel |
| | Merger | The combination of two or more companies into one company, where each company has equal power | NPS Pharmaceuticals and Enzon Pharmaceuticals, AstraZeneca |
| | Acquisition | When one company purchases another company in its entirety, and the acquiring company assumes full governance over the company acquired | Merck-Sirna |
| | Joint Venture | A new company created from the investment of resources of two companies | Alliance Boots and Guangzhou Pharmaceuticals Corp. |
| | Noncompetitive Collaboration | Two companies working together for the purpose of executing a particular business undertaking, but are not in competition with each other (usually in R&D collaborations) | Chugai with Dainippon Pharma with TA-270 |
| | License | The conditional rights to use an asset granted by the asset owner | Merck licenses PPL-100 from Ambrilia for an up-front fee, milestone fees, and royalties |
| Less Complex | Asset Purchase | Outright purchase of an asset | IDEC Pharma purchases 9-AC anticancer agent from Pharmacia |

Deal complexity is defined as the degree of collaboration between companies.

In one embodiment, the system 100 for predictive analytics using real-world pharmaceutical transactions shows unexpected and surprising results with respect to the second predictor (deal type) involving TRS (first measure of success). In the hierarchy of deal types, the common assumption has been that simple asset purchases or licensing deals are likely to create more value than more collaborative arrangements. Most licensing and business development executives prefer arms-length transactions with simpler deal terms. Research and Development executives similarly prefer the clarity of control that is associated with simpler deals.

However, the "simpler is better" assumption has not been confirmed by a rigorous study of the historical deal record. The system 100 for predictive analytics using real-world pharmaceutical transactions, and in particular, the predictive analytics engine 102, indicates that simpler transactions are not necessarily advantageous. Although a simpler deal may be less costly, easier to explain to management, and relatively easy to negotiate and manage, simple deals, such as licensing transactions, create less shareholder value for the buyer than more complex deals, such as collaborative arrangements. Simpler deals also have a lower probability of obtaining FDA approval ($p=0.06$ in Phase II, $p=0.20$ in Phase III).

More complex deals, such as collaborative arrangements, generally create higher shareholder value ($p=0.01$ in Phase I, $p=0.34$ in Phase II). For Phase I compounds, collaborative deals rather than simple licensing deals create more value for the buyer than other types of deals ($p=0.02$ for noncompetitive collaborations, $p=0.01$ for competitive collaborations). This may reflect that the seller in these collaborations is expressing confidence in the product but simply lacks some of the resources or capabilities needed to carry it to market.

The buying company's shareholders appear to suffer particularly from licensing deals for compounds in Phase II ($p=0.17$). For example, when Shire licensed Pyridorin in Phase II from BioStratum in November 2000 to develop an extended release version of the diabetic kidney disease drug, Shire shares lost 25.9 percent in value. Once reason for this occurrence is that in every deal there exists an imbalance of information. The seller almost always has more information than the buyer. Deals in which the seller insists on keeping "skin in the game" may signal the company's confidence in the asset. In such deals, the seller prefers risky profit sharing rather than safe, up-front cash and wants to remain involved in the product's development.

In contrast, a seller that prefers to off-load the product in an arms-length transaction, as in a simple licensing deal, is more likely to have negative information about the asset. What occurs in more complex collaborations is that the seller resolves the imbalance of information inherent in every deal. For that reason, these deal types are favored by the market and predict the likelihood of FDA approval.

With respect to the third predictor for success (compound type), the value that comes from a deal involving small or large molecule compounds depends on whether a company is the buyer or the seller. Deals for small molecule compounds are more likely to generate higher shareholder value for buyers ($p=0.29$, 0.20 for Phase I and Phase III respectively). Deals for large molecule compounds generate more value for sellers ($p=0.33$, 0.16 for Phase I and Phase II respectively). Small molecule drug are usually defined as a medicinal drug compound having a molecular weight of less than 1000 Daltons, and typically between 300 and 700 Daltons. These drugs are not made in living cells, but instead are made using highly reproducible processes involving chemical analysis. Small-molecule drugs are often defined completely by their atomic structure rather than by their manufacturing processes, and are administered orally in pill form. Large molecule drugs are usually defined as a drug with a molecular weight larger than 1000 Daltons. One example is biologics. Biologics are made through complex manufacturing processes that depend on biological organisms, e.g., yeast or bacteria. It is often difficult to directly compare one biotech product to another because the complexity of the manufacturing processes is central to the identity and characteristics of the final biological drug. Some examples of large molecule drugs include but are not limited to: proteins, antibodies, cytokines, hormones, and stem cells.

One reason underlying this surprising result may be that small molecule compounds are lower priced, while large molecule compounds demand a higher premium. To illustrate the different effects on the buyer of small vs. large molecule products, consider these examples. When Watson Pharmaceuticals bought Aslera, a Phase III small molecule compound for the treatment of lupus, from Genelabs, its shares gained an impressive 19.1 percent in value. But when Bristol-Myers Squibb bought Erbitux, a Phase III biologic compound for treatment of colorectal cancer from ImClone, Bristol-Myers Squibb's market value dropped 6.2 percent.

For sellers of small versus large molecule products, the reverse is true. For example, when Cypress Bioscience sold small molecule Milnacipran for fibromyalgia syndrome in Phase III to Forest Laboratories in 2004, Cypress Bioscience lost 24.1 percent in total shareholder return. Compare that to what happened to ImClone when it signed that deal to sell Erbitux, a biologic compound, to Bristol-Myers Squibb. The sale rewarded ImClone shareholders with a 31.8 percent increase in value.

Deals involving large molecule compounds are also less likely to receive FDA approval (p=0.26 in Phase II). Further, compounds out-licensed by biotechnology companies have a lower probability of gaining FDA approval than compounds out-licensed by pharmaceutical companies (p=0.08 for biotechnology out-licensing to biotechnology and p=0.25 for biotechnology out-licensing to pharmaceutical companies).

With respect to the fourth predictor for success (therapeutic area), the types of therapeutic areas are shown in Table 3 below:

TABLE 3

| Therapeutic Group* | Therapeutic Area |
| --- | --- |
| Group 1 | Allergy |
|  | Infection, |
|  | Anti-inflammatory |
|  | Pain |
|  | Dermatology |
| Group 2 | Cardiovascular |
| Group 3 | Respiratory |
| Group 4 | Blood Disease/Oncology |
| Group 5 | Gynecologic Oncology |
| Group 6 | Kidney |
|  | Liver |
|  | Metabolic |
|  | Transplantation |
| Group 7 | Other** |

*Each group also includes the autoimmune diseases of those therapeutic areas.
**This group includes therapeutic areas such as: central nervous system, gastrointestinal, ophthalmology and miscellaneous.

Group 4, Blood Disease/Oncology, is the therapeutic category most favored by the market, at least for early phase compounds (p=0.14 in Phase I). But when compounds in this therapeutic category are in the later stage, the market prefers other therapeutic areas, such as group 1 therapeutic category (Allergy/Infection/Anti-inflammatory/Pain/Dermatology) (where p=0.03, 0.23 for Phases II and III). For example, consider the Vitaxin deal in February 2001 when MedImmune and Targesome agreed to collaborate on a Phase I compound for targeted anticancer radiotherapy. MedImmune's shareholders enjoyed a 15.5 percent increase in value because of the purchase. Also, when Merck bought Phase I AGS-PSCA Antibody from Agensys for cancer therapy in 2005, Merck gained 7 percent in total shareholder return.

However, when Bristol-Myers Squibb bought the late-stage biologic compound, Erbitux, its shares lost 6.2 percent in value. Likewise, when Adherex Technologies bought Eniluracil to enhance the effectiveness of an oncology agent in Phase III from GlaxoSmithKline, Adherex lost 3.1 percent in TRS. In that deal, GlaxoSmithKline lost 5.3 percent in TRS.

The market very likely prefers certain therapeutic areas in early phases because riskier compounds with higher market potential, such as those in "blood disease/oncology" are more reasonably priced in these stages. But cancer drugs that have reached Phase III carry a heavy premium because they are highly sought after. The market does not reward buyers of these compounds, believing that the asset may be overpriced.

In deals for allergy/infection/anti-inflammatory/pain/dermatology compounds, the market is more likely to favor late stage deals. For compounds in these therapeutic areas, there is less unmet demand, so the product is more reasonably priced in later stages. This is understandable because those compounds may not be viewed as especially innovative or their market may be saturated.

In another embodiment, the system 100 for predictive analytics using real-world pharmaceutical transactions and/or the predictive analytics engine 102 have also identified the four predictors of a deal's success with respect to FDA approval (second measure of success). These four predictors or drivers of commercial success correlate positively with a higher probability of FDA approval.

With respect to the second measure of success (FDA approval) and the first predictor (phase), processing based on the above example using the transaction base of 18,194 (and subsequently reduced to eliminate non-compliant transactions, described below) determined that 28 compounds were approved vs. 17 terminated, or 62% of compounds in Phase III deals were approved (compounds in development or pending approval were excluded). For Phase II deals, 14 compounds were approved vs. 39 terminated, or 26% of compounds in Phase II deals were approved. Compare these percentages with industry success rates of Phase III, which have fallen from 75% to about 60% over the last 5 years, and compare to the industry success rates of Phase II, which have fallen from 40% to 25% over the last 5 years.

With respect to the second measure of success (FDA approval) and the second predictor (deal type), all deal types except for simple licensing deals correlate positively with an increased probability of FDA approval. Simple licensing deal have a negative correlation.

With respect to the second measure of success (FDA approval) and the third predictor (compound type), for Phase II deals, small molecule deals had a higher probability of FDA approval than biologics.

With respect to the second measure of success (FDA approval) and the fourth predictor (therapeutic area), for Phase III deals, all therapeutic areas except for Group 1 (Allergy/Pain/Infection), Group 4 (Blood Disease/Oncology), and Group 6 (Kidney/Liver/Metabolic) correlate positively with an increased probability of FDA approval. For Phase II deals, Group 1 (Allergy/Pain/Infection) deals have a higher probability of FDA approval than all other therapeutic areas.

Using logistic regression based on the predictors identified above, a probability of FDA approval can be determined. Table 4 below represents a spreadsheet for calculating a probability value for Phase II deals.

TABLE 4

PHASE II PROBABILITY PREDICTOR

| | A | B | C | D | E | F | G | H |
|---|---|---|---|---|---|---|---|---|
| 1 | | Probability Predictor | | | | | | |
| 2 | | | | | | | | |
| 3 | | Variable | Input Value | | Directions | | Parameter | Parameter Estimate |
| 4 | | DUM_CAA_PARTY_PHARMA | 1 | | -If CAA is 'Pharma', input 1, else input 0 | | Intercept | -0.0803 |
| 5 | | DUM_DT_LICENSE | 0 | | -If Deal type is 'License', input 1, else input 0 | | DUM_CAA_PARTY_PHARMA | 0.8876 |
| 6 | | DUM_TA_GROUP_1 | 0 | | -If TA Group is '1' input 1, else input 0 | | DUM_DT_LICENSE | -1.4923 |
| 7 | | DUM_TA_GROUP_4 | 1 | | -If TA Group is '4', input 1, else input 0 | | DUM_TA_GROUP_1 | 1.3226 |
| 8 | | DUM_BYSM_BIO | 1 | | -If Molecule Type is 'Biologic', input 1, else input 0 | | DUM_TA_GROUP_4 | 1.0592 |
| 9 | | TOTAL_TXN_FREQ_CAA | 1 | | -If CAA is 'Pharma', input 1, else input 0 | | DUM_BVSM_BIO | -1.2418 |
| 10 | | | | | | | TOTAL_TXN_FREQ_CAA | -0.0312 |
| 11 | | Probability | 64% | | | | | |
| 12 | | | | | | | | |
| 13 | | | | | | | | |

The spreadsheet formula for Cell C11 is shown below:

$$\text{EXP}(H4+\text{SUMPRODUCT}(C4:C9,H5:H10))/(1+\text{EXP}(H4+\text{SUMPRODUCT}(C4:C9,H5:H10)))$$

The above spreadsheet formula in cell C11 indicates that for the value of the variables shown, there is a 64% probability that FDA approval will be obtained. Logistic regression was performed on Phase II and Phase III data, and on the combined dataset. Depending on how the logistic regression is run, different regression equations emerge with distinct coefficients for the statistically significant variables. Such variables may be entered into column G with their coefficients entered into column H each time a logistic regression model for the dataset is created. The significance of this is 1) as more deal data is gathered, the predictor model becomes more accurate, and 2) depending on the dataset that is used for analysis, the key drivers of success for a deal may change. For example, if 10,000 more deals are added to the dataset, it is possible that other factors, such as, for example, prior relationship with partner, may become statistically significant and may become a key success driver in deals. The formula is in the form of $e^x/(1+e^x)$, where "x" is the intercept value plus the sum of products. The descriptions of the variables in cells B4-B9 are shown in Table 5 below. The corresponding parameter values are located in cells H5-H9, and the intercept value is located in cell H4:

TABLE 5

| VARIABLE NAME | DESCRIPTION |
|---|---|
| DUM_CAA_PARTY_PHARMA | The input value of 1 in cell C4 indicates a pharmaceutical deal. |
| DUM_DT_LICENSE | The input value of 0 in cell C5 indicates that this is not a licensing deal. |
| DUM_TA_GROUP_1 | The input value of 0 in cell C6 indicates that the deal does not involve therapeutic group 1, as shown above in Table 3 |
| DUM_TA_GROUP_4 | The input value of 1 in cell C7 indicates that the deal does involve therapeutic group 1, as shown above in Table 3. |
| DUM_BVSM_BIO | The input value of 1 in cell C8 indicates that the compound is biologic. |
| TOTAL_TXN_FREQ_CAA | The input value of 1 in cell C9 indicates a pharmaceutical deal. |

Table 6 below represents a spreadsheet for calculating a probability value for Phase III deals. The spreadsheet formula is the same as shown above:

TABLE 6

PHASE III PROBABILITY PREDICTOR

| A | B | C | D | E | F | G | H |
|---|---|---|---|---|---|---|---|
| 1 | Probability Predictor | | | | | | |
| 2 | | | | | | | |
| 3 | Variable | Input Value | | Directions | | Parameter | Parameter Estimate |
| 4 | DUM_CWA_PARTY_BIOTEC | 1 | | -If CWA is 'Biotech' input 1, else input 0 | | Intercept | 3.4871 |
| 5 | DUM_DT_LICENSE | 1 | | -If Deal Type is 'License', input 1, else input 0 | | DUM_CWA_PARTY_BIOTEC | -0.8711 |
| 6 | WEAKNESS_OF_INCENTIVE | 0.26 | | -Enter in weakness of incentive (bet. 0 and 1, average is 0.26) | | DUM_DT_LICENSE | -1.1364 |
| 7 | DUM_TA_GROUP_1 | 1 | | -If TA Group is '1', input 1, else input 0 | | WEAKNESS_OF_INCENTIVE | -1.688 |
| 8 | DUM_TA_GROUP_4 | 0 | | -If TA Group is '4', input 1, else input 0 | | DUM_TA_GROUP_1 | -1.0772 |
| 9 | DUM_TA_GROUP_6 | 0 | | -If TA Group is '6', input 1, else input 0 | | DUM_TA_GROUP_4 | -2.1325 |
| 10 | | | | | | DUM_TA_GROUP_6 | -1.9565 |
| 11 | Probability | 49% | | | | | |
| 12 | | | | | | | |

The above spreadsheet formula in cell C11 indicates that for the value of the variables shown, there is a 49% probability that FDA approval will be obtained. The formula is in the form of $e^x/(1+e^x)$, where "x" is the intercept value plus the sum of products. The descriptions of the variables in cells B4-B9 are shown in Table 7 below. The corresponding parameter values are located in cells H5-H9, and the intercept value is located in cell H4:

TABLE 7

| VARIABLE NAME | DESCRIPTION |
|---|---|
| DUM_CAA_PARTY_BIOTEC | The input value of 1 in cell C4 indicates a biotechnology deal. |
| DUM_DT_LICENSE | The input value of 1 in cell C5 indicates that this is not a licensing deal. |
| WEAKNESS_OF_INCENTIVE | The input value of 0.26 in cell C6 indicates an average value of the incentive |
| DUM_TA_GROUP_1 | The input value of 1 in cell C7 indicates that the deal does involve therapeutic group 1, as shown above in Table 3. |
| DUM_TA_GROUP_4 | The input value of 0 in cell C8 indicates that the deal does not involve therapeutic group 4, as shown above in Table 3. |
| DUM_TA_GROUP_6 | The input value of 0 in cell C9 indicates that the deal does not involve therapeutic group 6, as shown above in Table 3. |

In one example, the system 100 for predictive analytics using real-world pharmaceutical transactions may process a large number of pharmaceutical deals or transactions. The number of deals analyzed may be reduced to exclude non-compliant deals. In one specific example, the data collection component 106 inspected data from 18,194 deals during a ten-year period from about 1997 to about 2006. Data was extracted from Recombinant Capital's rDNA's database. The data reduction module 108 eliminated non-compliant transactions to generate a reduced transaction data set. Data regarding total return to shareholders was obtained from the Center for Research in Security Prices (CRSP) and Yahoo! Finance.

With regard to the first measure of success (TRS) and application of multiple linear regression, certain non-compliant deals were excluded to obtain the reduced transaction data set, as shown in Table 8 below. In this specific example, the initial data set of 18,194 deals was reduced to about 355 deals before applying statistical analyses. For the deals that had TRS information, multiple linear regression was applied to measure the magnitude of excess TRS. For the deals in Phase II and Phase III that had approval information (approved or rejected), logistic regression was applied to measure the likelihood of eventual FDA approval.

TABLE 8

| | |
|---|---|
| International | International deals directed to development or commercialization outside of the U.S. were excluded. Of these deals, those that also had development or commercialization inside the U.S. were not excluded |
| Multiple Phase | Deals where compounds were in multiple phases were excluded to permit more cogent insight about inter-phase differences. |
| Drugs Approved | Drugs that already received FDA approval were excluded |
| Parties | Deals not between pharmaceutical companies and biotechnology companies were excluded |
| Stock Information | Deals where companies that were not listed on a stock exchange or did not have stock price information available were excluded. |
| Manufacturing | Deals for manufacturing or contract research organization services were excluded |

With regard to the second measure of success (FDA approval) and application of a logistic regression process to determine the type of deal that positively correlates with FDA approval, deals with "ongoing research" or "pending FDA approval" were excluded. An FDA response was required to serve as the dependant variable. The reduced transaction data set corresponding to the second measure of success was augmented with drug approval data from Drugs@FDA. Note that the reduced transaction data set used in determining the first measure of success (TRS) may have a different size than the reduced transaction data set used in determining the second measure of success (FDA approval) due to the different exclusion criteria.

The report generator 109 (FIG. 1) provides a graphical or hard copy output indicating the predictors or success, excess total return to shareholders, and/or the probability value associated with the likelihood of FDA approval.

Note that although the system 100 for predictive analytics using real-world pharmaceutical transactions and/or the predictive analytics engine 102 predicts success of a deal based on FDA approval as one measure, any regulatory body approval may be used as the measure. Accordingly, other regulatory agencies may include the Therapeutic Goods Administration (TGA-Australia), the European Medicines Agency (EMEA-European Union), the Japan Ministry of Health, Labour, and Welfare (MHLW), and the like.

The predictors of success determined by the system 100 for predictive analytics using real-world pharmaceutical transactions are in some instances, surprising, unexpected, and counter-intuitive. For example, the analysis results indicate that competitive collaborations, not simple licensing deals, are most likely to increase shareholder value and gain FDA approval. Other analysis results indicate that the stock market clearly rewards buyers of Phase III compounds. However, the analysis results also indicate that there is no correlation between an enthusiastic market reaction and eventual FDA approval. This is surprising and counter-intuitive.

Further, when considering what is good for a buyer versus what is good for a seller in the making of a pharmaceutical deal, the answer depends on whether the deal is for a small or a large molecule compound. Accordingly, the system 100 for predictive analytics using real-world pharmaceutical transactions can assess a deal's potential for success, and it can provide insight on how a strategic approach to licensing and business development can increase a company's competitive power and accelerate its drive for high performance.

The predictors of success determined by the system 100 for predictive analytics using real-world pharmaceutical transactions can maximize shareholder value through licensing and business development investments and improve the effectiveness of a company's licensing and business development strategy by sharpening the ability to select from the prospects at hand. A company may do this in a short-term timeframe and in a long-term timeframe.

In the short term, the most effective way for companies to drive shareholder value and improve the likelihood of FDA approval is to form collaborative partnerships (second predictor). The success of these collaborations is attributed to the confidence in the product expressed by the seller's willingness to put "skin in the game."

In the longer term, evaluation of the results is more complex. If the level of investment required to acquire attractive product innovations continues to grow at the current rate, many companies will find themselves in an "arms race" of continual escalation of licensing and business development investments, and participation in this race soon becomes unfeasible. Thus, companies must be skillful in choosing the right deals, and must make difficult and judicious choices about which deals to pursue.

However, in the deal selection process what is good for the buyer may be different from what is good for the seller. Results from the system 100 for predictive analytics using real-world pharmaceutical transactions in one embodiment indicate that buyers should take the following actions:

1. Seek sellers who want to partner in the development or commercialization of the compound. This signals a high degree of confidence in the asset, and is especially important in late-stage products.
2. Consider buying Phase III compounds if they can be found, but approach these expensive deals cautiously. While these purchases increase shareholder value in the short term, there is no correlation between the market's enthusiasm and FDA approval for Phase III products.
3. Buy blood disease/oncology products in Phase I. But be judicious in later phases of development when these products command a much higher premium.
4. Buy allergy/infection/anti-inflammatory/pain/dermatology compounds in later phases of development. At this point they are reasonably priced and have lower risk.
5. Be cautious about large molecule compounds because of their high prices.

Results from the system 100 for predictive analytics using real-world pharmaceutical transactions in one embodiment indicate that sellers should take the following actions:

1. Raise the price of Phase III compounds even more. The market is willing to reward buyers at this point and sellers should factor that into the price.
2. Sell large molecule compounds in Phases I and II of development.

The results shown in the following tables (Table 9-Table 19) may be generated by the comparator module 105 of the predictive analytics engine 102. Table 9 provides a summary illustrating how buyers can maximize TRS with regard to phase I deals. The table indicates whether TRS increases or decreases based on the illustrated factors, and provides a corresponding confidence level.

TABLE 9

Does the Total Return to Shareholders to the BUYER increase or decrease?

| Factors | Phase 1 | P-Value |
|---|---|---|
| Deal Type: License | ▲ | 0.01 |
| Deal Type: Non-Competitive Collaboration | ▲ | 0.02 |
| Deal Type: Competitive Collaboration | ▲ | 0.01 |
| TA: Blood/Oncology | ▲ | 0.14 |
| TA: Allergy/Pain/Infection | N/A | N/A |
| Compound Type: Small Molecule | ▲ | 0.29 |

Note:
N/A denotes factor not statistically significant for that phase.

Table 10 provides a summary illustrating how buyers can maximize TRS with regard to phase II deals. The table indicates whether TRS increases or decreases based on the illustrated factors, and provides a corresponding confidence level.

TABLE 10

Does the Total Return to Shareholders to the BUYER increase or decrease?

| Factors | Phase 2 | P-Value |
|---|---|---|
| Deal Type: License | ↓ | 0.17 |
| Deal Type: Non-Competitive Collaboration | N/A | N/A |
| Deal Type: Competitive Collaboration | N/A | N/A |
| TA: Blood/Oncology | N/A | N/A |
| TA: Allergy/Pain/Infection | ▲ | 0.03 |
| Compound Type: Small Molecule | N/A | N/A |

Note:
N/A denotes factor not statistically significant for that phase.

Table 11 provides a summary illustrating how buyers can maximize TRS with regard to phase III deals. The table indicates whether TRS increases or decreases based on the illustrated factors, and provides a corresponding confidence level.

TABLE 11

Does the Total Return to Shareholders to the BUYER increase or decrease?

| Factors | Phase 3 | P-Value |
|---|---|---|
| Phase: Phase 3 | ▲ | 0.09* |
| Deal Type: License | N/A | N/A |
| Deal Type: Non-Competitive Collaboration | N/A | N/A |
| Deal Type: Competitive Collaboration | ▲ | 0.34 |
| TA: Blood/Oncology | N/A | N/A |
| TA: Allergy/Pain/Infection | ▲ | 0.23 |
| Compound Type: Small Molecule | ▲ | 0.20 |

Note:
N/A denotes factor not statistically significant for that phase.
*Very limited evidence, model with all combined phases had a poor fit.

Table 12 provides a summary illustrating how buyers can maximize TRS with regard to phase I, II, and III deals. The table indicates whether TRS increases or decreases in the specific phase based on the illustrated factors, and provides a corresponding confidence level.

TABLE 12

Does the Total Return to Shareholders to the BUYER increase or decrease?

| Factors | Phase 1 | Phase 2 | Phase 3 | P-Value |
|---|---|---|---|---|
| Phase: Phase 1 vs. 2 vs. 3 | N/A | N/A | ▲ | 0.09* |
| Deal Type: License | ▲ | ↓ | N/A | 0.01, 0.17 |
| Deal Type: Non-Competitive Collaboration | ▲ | N/A | N/A | 0.02 |
| Deal Type: Competitive Collaboration | ▲ | N/A | ▲ | 0.01, 0.34 |
| TA: Blood/Oncology | ▲ | N/A | N/A | 0.14 |
| TA: Allergy/Pain/Infection | N/A | ▲ | ▲ | 0.03, 0.23 |
| Compound Type: Small Molecule | ▲ | N/A | ▲ | 0.29, 0.20 |

*Very limited evidence, model with all combined phases had a poor fit.
Note:
N/A denotes factor not statistically significant for that phase.

Table 13 provides a summary illustrating how sellers can maximize TRS with regard to phase I deals. The table indicates whether TRS increases or decreases based on the illustrated factors, and provides a corresponding confidence level.

TABLE 13

Does the Total Return to Shareholders to the SELLER increase or decrease?

| Factors | Phase 1 | P-Value |
|---|---|---|
| Phase: Phase 1 | ↓ | 0.03 |
| Deal Type: Competitive Collaboration | ↓ | 0.29 |
| Deal Type: Non-Competitive Collaboration | N/A | N/A |
| TA: Allergy/Pain/Infection | ↓ | 0.02 |
| TA: Blood/Oncology | ↓ | 0.02 |
| TA: Kidney/Liver/Metabolic | ↓ | 0.08 |
| Compound Type: Biologic | ▲ | 0.33 |
| Deal Size: Larger | ▲ | 0.03 |

Note:
N/A denotes factor not statistically significant for that phase.
Phase I and Phase II both have a negative influence on TRS, but Phase I creates even less value than Phase II.

Table 14 provides a summary illustrating how sellers can maximize TRS with regard to phase II deals. The table indicates whether TRS increases or decreases based on the illustrated factors, and provides a corresponding confidence level.

TABLE 14

Does the Total Return to Shareholders to the SELLER increase or decrease?

| Factors | Phase 2 | P-Value |
|---|---|---|
| Phase: Phase 2 | ↓ | 0.03 |
| Deal Type: Competitive Collaboration | N/A | N/A |
| Deal Type: Non-Competitive Collaboration | ↓ | 0.02 |
| TA: Allergy/Pain/Infection | N/A | N/A |
| TA: Blood/Oncology | N/A | N/A |
| TA: Kidney/Liver/Metabolic | N/A | N/A |
| Compound Type: Biologic | ▲ | 0.16 |
| Deal Size: Larger | N/A | N/A |

Note:
N/A denotes factor not statistically significant for that phase.
Phase I and Phase II both have a negative influence on TRS, but Phase I creates even less value than Phase II.

Table 15 provides a summary illustrating how sellers can maximize TRS with regard to phase III deals. The table indicates whether TRS increases or decreases based on the illustrated factors, and provides a corresponding confidence level.

TABLE 15

Does the Total Return to Shareholders to the SELLER increase or decrease?

| Factors | Phase 3* | P-Value |
|---|---|---|
| Phase: Phase 3 | N/A | N/A |
| Deal Type: Competitive Collaboration | N/A | N/A |
| Deal Type: Non-Competitive Collaboration | N/A | N/A |
| TA: Allergy/Pain/Infection | ↓ | 0.15 |
| TA: Blood/Oncology | ↓ | 0.11 |
| TA: Kidney/Liver/Metabolic | N/A | N/A |
| Compound Type: Biologic | N/A | N/A |
| Deal Size: Larger | N/A | N/A |

Note:
N/A denotes factor not statistically significant for that phase.
*Very limited evidence, as Phase III seller model had a poor fit.

Table 16 provides a summary illustrating how sellers can maximize TRS with regard to phase I, II, and III deals. The table indicates whether TRS increases or decreases in the specific phase based on the illustrated factors, and provides a corresponding confidence level.

TABLE 16

Does the Total Return to Shareholders to the SELLER increase or decrease?

| Factors | Phase 1 | Phase 2 | Phase 3* | P-Value |
|---|---|---|---|---|
| Phase: Phase 1 vs. 2 vs. 3 | ↓ | ↓ | N/A | 0.03, 0.03 |
| Deal Type: Competitive Collaboration | ↓ | N/A | N/A | 0.29 |
| Deal Type: Non-Competitive Collaboration | N/A | ↓ | N/A | 0.02 |
| TA: Allergy/Pain/Infection | ↓ | N/A | ↓ | 0.02, 0.15 |
| TA: Blood/Oncology | ↓ | N/A | ↓ | 0.02, 0.11 |
| TA: Kidney/Liver/Metabolic | ↓ | N/A | N/A | 0.08 |
| Compound Type: Biologic | ▲ | ▲ | N/A | 0.33, 0.16 |
| Deal Size: Larger | ▲ | N/A | N/A | 0.03 |

*Very limited evidence, as Phase III seller model had a poor fit.
Note:
N/A denotes factor not statistically significant for that phase.

Table 17 provides a summary illustrating the factors that influence the probability of drug approval with regard to phase II deals. The table indicates whether the probability increases or decreases based on the illustrated factors, and provides a corresponding confidence level.

TABLE 17

Does the Probability of Drug Approval increase or decrease with each factor?

| Factors | Phase 2 | P-Value |
|---|---|---|
| Phase: Phase 2 vs. Phase 3 | ↓ | 0.0005 |
| Deal Type: License | ↓ | 0.06 |
| TA: Allergy/Pain/Infection | ↑ | 0.20 |
| TA: Blood/Oncology | ↑ | 0.30 |
| TA: Kidney/Liver/Metabolic | N/A | N/A |
| Compound Type: Biologic | ↓ | 0.26 |

Note:
Logistic regression not performed for Phase I deals; N/A denotes factor not statistically significant for that phase.

Table 18 provides a summary illustrating the factors that influence the probability of drug approval with regard to phase III deals. The table indicates whether the probability increases or decreases based on the illustrated factors, and provides a corresponding confidence level.

TABLE 18

Does the Probability of Drug Approval increase or decrease with each factor?

| Factors | Phase 3 | P-Value |
|---|---|---|
| Phase: Phase 3 | N/A | N/A |
| Deal Type: License | ↓ | 0.20 |
| TA: Allergy/Pain/Infection | ↓ | 0.19 |
| TA: Blood/Oncology | ↓ | 0.03 |
| TA: Kidney/Liver/Metabolic | ↓ | 0.17 |
| Compound Type: Biologic | N/A | N/A |

Note:
Logistic regression not performed for Phase I deals;

N/A denotes factor not statistically significant for that phase.

Table 19 provides a summary illustrating the factors that influence the probability of drug approval with regard to in-licensed deals for phase II and phase III. The table indicates whether the probability increases or decreases based on the illustrated factors, and provides a corresponding confidence level.

TABLE 19

Does the Probability of Drug Approval increase or decrease with each factor?

| Factors | Phase 2 | Phase 3 | P-Value |
|---|---|---|---|
| Phase: Phase 2 vs. Phase 3 | ↓ | N/A | 0.0005 |
| Deal Type: License | ↓ | ↓ | 0.06, 0.20 |
| TA: Allergy/Pain/Infection | ↑ | ↓ | 0.20, 0.19 |
| TA: Blood/Oncology | ↑ | ↓ | 0.30, 0.03 |
| TA: Kidney/Liver/Metabolic | N/A | ↓ | 0.17 |
| Compound Type: Biologic | ↓ | N/A | 0.26 |

Note:
Logistic regression not performed for Phase I deals;
N/A denotes factor not statistically significant for that phase.

Figure 5:
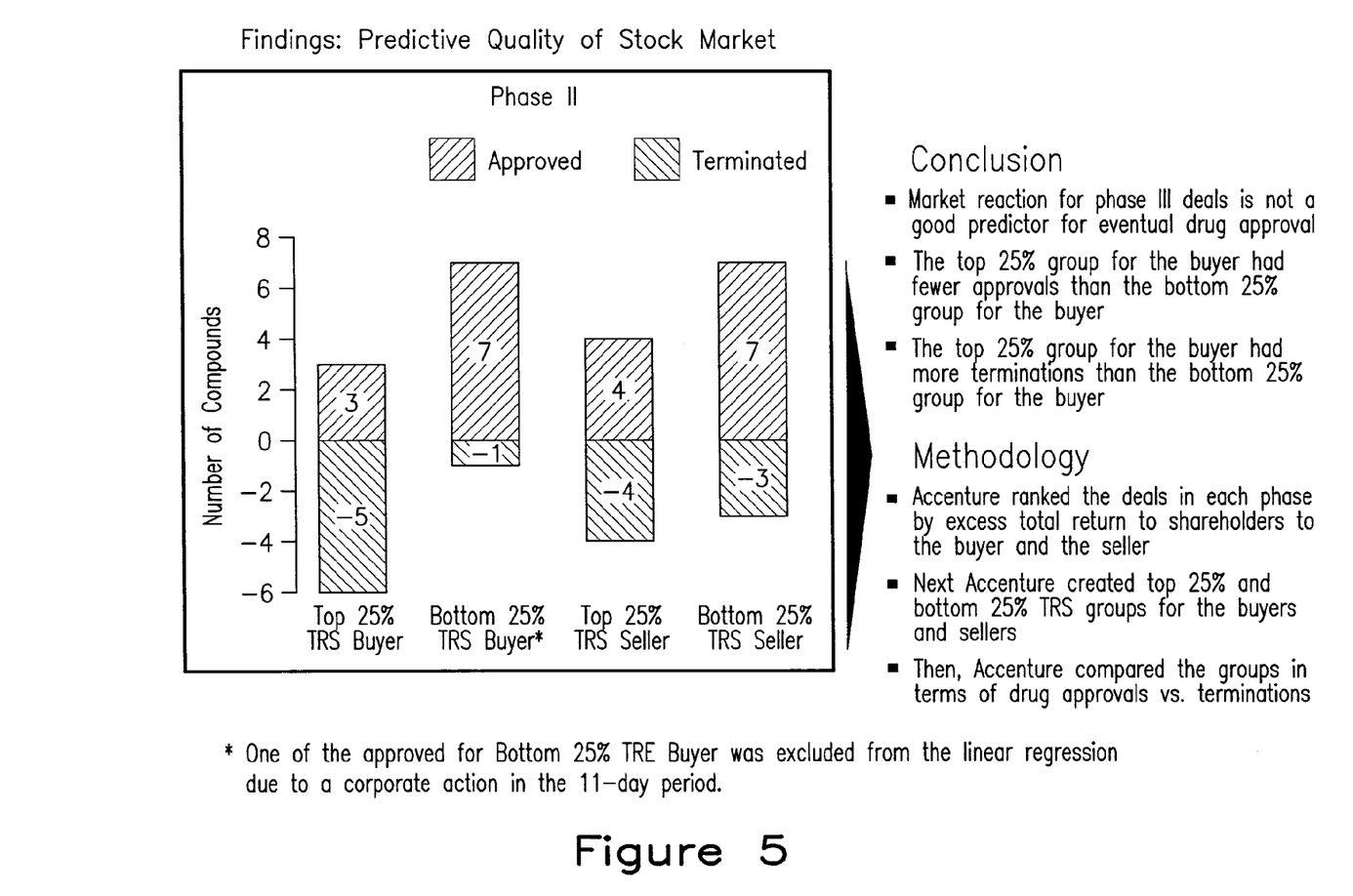
FIG. 5 is a graph illustrating the predictive quality of the stock market for phase III compounds.

FIG. 5 graphically illustrates that higher shareholder return is not necessarily a good predictor of eventual FDA approval for phase III compounds. For example, the deals having the top 25% in TRS had fewer FDA approvals than deals in the bottom 25% in TRS.

Figure 6:
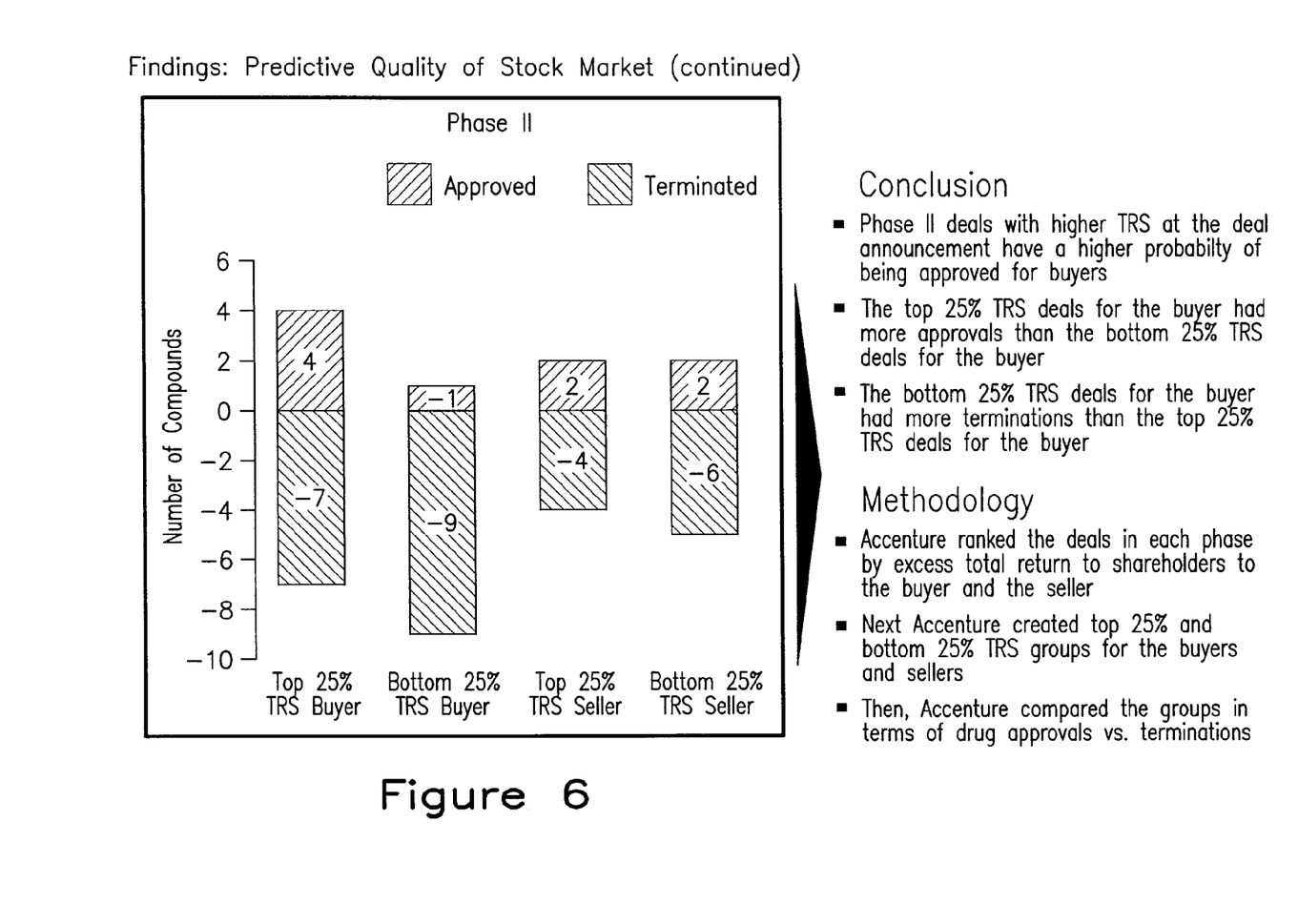
FIG. 6 is a graph illustrating the predictive quality of the stock market for phase II compounds.

However, FIG. 6 graphically illustrates that for phase II deals, a much stronger link between market reaction at the time of deal announcement and the likelihood of FDA approval exists. In this case, for example, the deals having the top 25% in TRS had a greater number of FDA approvals than deals in the bottom 25% in TRS.

The logic, circuitry, and processing described above may be encoded in a computer-readable medium such as a CDROM, disk, flash memory, RAM or ROM, an electromagnetic signal, or other machine-readable medium as instructions for execution by a processor. Alternatively or additionally, the logic may be implemented as analog or digital logic using hardware, such as one or more integrated circuits, or one or more processors executing instructions; or in software in an application programming interface (API) or in a Dynamic Link Library (DLL), functions available in a shared memory or defined as local or remote procedure calls; or as a combination of hardware and software.

The logic may be represented in (e.g., stored on or in) a computer-readable medium, machine-readable medium, propagated-signal medium, and/or signal-bearing medium. The media may comprise any device that contains, stores, communicates, propagates, or transports executable instructions for use by or in connection with an instruction executable system, apparatus, or device. The machine-readable medium may selectively be, but is not limited to, an electronic, magnetic, optical, electromagnetic, or infrared signal or a semiconductor system, apparatus, device, or propagation medium. A non-exhaustive list of examples of a machine-readable medium includes: a magnetic or optical disk, a volatile memory such as a Random Access Memory "RAM," a Read-Only Memory "ROM," an Erasable Programmable Read-Only Memory (i.e., EPROM) or Flash memory, or an optical fiber. A machine-readable medium may also include a tangible medium upon which executable instructions are printed, as the logic may be electronically stored as an image or in another format (e.g., through an optical scan) and then compiled and/or interpreted or otherwise processed. The processed medium may then be stored in a computer and/or machine memory.

The systems may include additional or different logic and may be implemented in many different ways. A controller may be implemented as a microprocessor, microcontroller, application specific integrated circuit (ASIC), discrete logic, or a combination of other types of circuits or logic. Similarly, memories may be DRAM, SRAM, Flash, or other types of memory. Parameters (e.g., conditions and thresholds) and other data structures may be separately stored and managed, may be incorporated into a single memory or database, or may be logically and physically organized in many different ways. Programs and instruction sets may be parts of a single program, separate programs, or distributed across several memories and processors.

While various embodiments of the invention have been described, it will be apparent to those of ordinary skill in the art that many more embodiments and implementations are possible within the scope of the invention. Accordingly, the invention is not to be restricted except in light of the attached claims and their equivalents.

We claim:

1. A system for predictive analytics for a target entity using real-world pharmaceutical transactions, comprising:
a computer having a processor and memory;
a data collection component controlled by the processor, configured to aggregate data for a plurality of pharmaceutical transactions external to the target entity, the aggregate data corresponding to publicly-traded financial data based upon a predetermined time period surrounding a public announcement of the respective pharmaceutical transaction;
a data reduction module controlled by the processor, configured to eliminate non-compliant transactions to generate a reduced transaction data set;
an analysis module controlled by the processor, configured to apply multiple linear regression analysis to a first portion of the reduced transaction data set to identify key regression variables that correlate with an excess total return to shareholders;
the analysis module configured to apply logistic regression analysis to a second portion of the reduced transaction data set to identify key regression variables that correlate with an increased probability of regulatory agency approval;
the key regression variables including
drug clinical trial phase including phase I trials, phase II trials, and phase III trials;
deal type;
compound type, which indicates whether the respective pharmaceutical transaction involves a small molecule compound having a molecular weight of less than or equal to 1000 Daltons or a large molecule compound having a molecular weight greater than 1000 Daltons; and
therapeutic area;
a comparator module that based on the regression analysis applied, determines that:
an increased total return to shareholders for a buyer correlates with a respective pharmaceutical transaction involving the phase III trial;
an increased total return to shareholders for a buyer correlates with a respective pharmaceutical transaction involving a phase I trial wherein the deal type is a license, a non-competitive collaboration, or a competitive collaboration;
a decreased total return to shareholders for a buyer correlates with a respective pharmaceutical transaction involving a phase II trial wherein the deal type is the license; and
a report generator adapted to provide a graphical output of the identified key regression variables and an indication of the corresponding effect on total return to shareholders, and a probability value corresponding to a likelihood of regulatory agency approval.

2. The system according to claim 1, wherein the predetermined time period is an eleven day time period.

3. The system according to claim 1, wherein the predetermined time period ranges from one week to one month.

4. The system according to claim 1, wherein the predetermined time period is less than one year.

5. The system according to claim 1, wherein the non-compliant transactions are selected from the group consisting of international deals, dealing with multiple phase compounds, drugs having regulatory body approval, deals not between pharmaceutical companies and biotechnology companies, deals involving companies not listed on a stock exchange, and deals directed to manufacturing.

6. The system according to claim 1, wherein the drug clinical trial phase indicates whether the respective pharmaceutical transaction involves drugs currently in phase I clinical trials, phase II clinical trials, or phase III clinical trials.

7. The system according to claim 1, wherein the deal type corresponds to a level of collaboration between parties to a respective transaction.

8. The system according to claim 7, wherein the comparator module determines that:
an increased total return to shareholders for a buyer correlates with a respective pharmaceutical transaction involving a phase I compound where a level of collaboration includes a license, a non-competitive collaboration, and a competitive collaboration;
an increased total return to shareholders for a buyer correlates with a respective pharmaceutical transaction involving a phase III compound where a level of collaboration is the competitive collaboration;
a decreased total return to shareholders for a buyer correlates with a respective pharmaceutical transaction involving a phase II compound where a level of collaboration is the license;
a total return to shareholders for a buyer does not correlate with a respective pharmaceutical transaction involving a phase II compound where a level of collaboration is the non-competitive collaboration or the competitive collaboration; and
a total return to shareholders for a buyer does not correlate with a respective pharmaceutical transaction involving a phase III compound where a level of collaboration is the non-competitive collaboration or the license.

9. The system according to claim 7, wherein the comparator module determines that:
a decreased total return to shareholders for a seller correlates with a respective pharmaceutical transaction involving a phase I compound where a level of collaboration is a competitive collaboration;
a decreased total return to shareholders for a seller correlates with a respective pharmaceutical transaction involving a phase II compound where a level of collaboration is a non-competitive collaboration;
a total return to shareholders for a seller does not correlate with a respective pharmaceutical transaction involving a phase II compound or a phase III compound where a level of collaboration is the competitive collaboration; and
a total return to shareholders for a seller does not correlate with a respective pharmaceutical transaction involving a phase I compound or a phase III compound where a level of collaboration is the non-competitive collaboration.

10. The system according to claim 1, wherein the therapeutic area indicates whether the respective pharmaceutical transaction involves a group 1 therapeutic area (allergy/infection/anti-inflammatory/pain/dermatology), a group 2 therapeutic area (cardiovascular), a group 3 therapeutic area (respiratory), a group 4 therapeutic area (blood disease/oncology), a group 5 therapeutic area (gynecologic oncology), a group 6 therapeutic area (kidney/liver/metabolic), or a group 7 therapeutic area (autoimmune diseases of groups 1-6).

11. The system according to claim 10, wherein the comparator module determines that:
an increased total return to shareholders for a buyer correlates with a respective pharmaceutical transaction involving a phase I compound where the therapeutic area is a group 4 therapeutic area;
an increased total return to shareholders for a buyer correlates with a respective pharmaceutical transaction involving a phase II compound or a phase III compound, where the therapeutic area is a group 1 therapeutic area;
a total return to shareholders for a buyer does not correlate with a respective pharmaceutical transaction involving a phase II compound or a phase III compound, where the therapeutic area is a group 4 therapeutic area; and a total return to shareholders for a buyer does not correlate with a respective pharmaceutical transaction involving a phase I compound where the therapeutic area is a group 1 therapeutic area.

12. The system according to claim 1, wherein the comparator module determines that:
an increased total return to shareholders for a buyer correlates with a respective pharmaceutical transaction involving a phase III compound; and
a total return to shareholders for a buyer has no correlation for a respective pharmaceutical transaction involving a phase II compound or a phase III compound.

13. The system according to claim 1, wherein the comparator module determines that:
an increased total return to shareholders for a buyer correlates with a respective pharmaceutical transaction involving a phase I compound or a phase III compound where the compound type is a small molecule compound; and
a total return to shareholders for a buyer does not correlate with a respective pharmaceutical transaction involving a phase II compound where the compound type is a small molecule compound.

14. The system according to claim 1, wherein the comparator module determines that:
a decreased total return to shareholders for a seller correlates with a respective pharmaceutical transaction involving a phase II compound or a phase III compound; and
a total return to shareholders for a seller does not correlate with a respective pharmaceutical transaction involving a phase III compound.

15. A method for predictive analytics for a target entity using real-world pharmaceutical transactions, comprising:
providing a computer having a processor and memory;
collecting, by the processor, data for a plurality of pharmaceutical transactions external to the target entity, the aggregate data corresponding to publicly-traded financial data based upon a predetermined time period surrounding a public announcement of the respective pharmaceutical transaction;
eliminating non-compliant transactions from the plurality of pharmaceutical transactions to generate a reduced transaction data set;
applying multiple linear regression, by the processor, to a first portion of the reduced transaction data set to identify key regression variables that correlate with an excess total return to shareholders;
applying logistic regression analysis, by the processor, to a second portion of the reduced transaction data set to identify key regression variables that correlate with an increased probability of regulatory agency approval;
the key regression variables including
drug clinical trial phase including phase I trials, phase II trials, and phase III trials;
deal type;
compound type, which indicates whether the respective pharmaceutical transaction involves a small molecule compound having a molecular weight of less than or equal to 1000 Daltons or a large molecule compound having a molecular weight greater than 1000 Daltons;
therapeutic area;
determining, by the processor, using the regression analysis that:

an increased total return to shareholders for a buyer correlates with a respective pharmaceutical transaction involving the phase III trial;
an increased total return to shareholders for a buyer correlates with a respective pharmaceutical transaction involving a phase I trial wherein the deal type is a license, a non-competitive collaboration, or a competitive collaboration;
a decreased total return to shareholders for a buyer correlates with a respective pharmaceutical transaction involving a phase II trial wherein the deal type is the license; and
generating a graphical output of the identified key regression variables and an indication of the corresponding effect on total return to shareholders, and a probability value corresponding to a likelihood of regulatory agency approval.

16. The method according to claim 15, wherein the regulatory agency is the U.S. Food and Drug Administration (FDA), Therapeutic Goods Administration (TGA-Australia), the European Medicines Agency (EMEA-European Union), or the Japan Ministry of Health, Labour, and Welfare (MHLW).

17. The method according to claim 15, further determining that:
a probability of receiving the regulatory body approval for phase II compounds negatively correlates with a respective pharmaceutical transaction when a level of collaboration between parties of the transaction is a license;
a probability of receiving the regulatory body approval for phase II compounds positively correlates with a respective pharmaceutical transaction when a therapeutic area of the transaction is group 1 therapeutic area (allergy/infection/anti-inflammatory/pain/dermatology) or a group 4 therapeutic area (blood disease/oncology)
a probability of receiving the regulatory body approval for phase II compounds negatively correlates with a respective pharmaceutical transaction when the transaction deals with biologic compounds; and
a probability of receiving the regulatory body approval for phase II compounds does not correlates with a respective pharmaceutical transaction when the therapeutic area of the transaction is a group 6 therapeutic area (kidney/liver/metabolic).

18. The method according to claim 15, further determining that:
a probability of receiving the regulatory body approval for phase III compounds negatively correlates with a respective pharmaceutical transaction when a level of collaboration between parties of the transaction is a license;
a probability of receiving the regulatory body approval for phase III compounds negatively correlates with a respective pharmaceutical transaction when a therapeutic area of the transaction is a group 1 therapeutic area (allergy/infection/anti-inflammatory/pain/dermatology), a group 4 therapeutic area (blood disease/oncology), or a group 6 therapeutic area (kidney/liver/metabolic); and
a probability of receiving the regulatory body approval for phase III compounds does not correlate with a respective pharmaceutical transaction when the transaction deals with biologic compounds.

* * * * *